(12) United States Patent
Pourati et al.

(10) Patent No.: US 12,274,453 B2
(45) Date of Patent: Apr. 15, 2025

(54) METHOD OF DRILLING HOLES IN BONES AND HARVESTING BONE FRAGMENTS FOR BONE GRAFTING

(71) Applicant: Jacob Pourati, Brookline, MA (US)

(72) Inventors: Jacob Pourati, Brookline, MA (US); Daniel M Schaner, Billings, MT (US)

(*) Notice: Subject to any disclaimer, the term of this patent is extended or adjusted under 35 U.S.C. 154(b) by 381 days.

(21) Appl. No.: 17/987,196

(22) Filed: Nov. 15, 2022

(65) Prior Publication Data
US 2024/0156471 A1   May 16, 2024

(51) Int. Cl.
*A61B 17/16* (2006.01)

(52) U.S. Cl.
CPC ...... *A61B 17/1635* (2013.01); *A61B 17/1615* (2013.01)

(58) Field of Classification Search
CPC . A61B 17/16; A61B 17/1613; A61B 17/1615; A61B 17/162; A61B 17/1622; A61B 17/1624; A61B 17/1626; A61B 17/1628; A61B 17/1635; A61B 17/1662; A61B 17/1673; A61C 1/02; A61C 1/04; A61C 1/05; A61C 1/06; A61C 3/02; A61C 3/025
See application file for complete search history.

(56) References Cited

U.S. PATENT DOCUMENTS

| | | | |
|---|---|---|---|
| 1,643,679 A | 9/1927 | Roderick | |
| 3,645,642 A | 2/1972 | Koslow | |
| 3,667,857 A | 6/1972 | Shaner et al. | |
| 4,345,899 A | 8/1982 | Vlock | |
| 4,662,803 A | 5/1987 | Arnold | |
| 4,913,603 A | 4/1990 | Friedli et al. | |
| 5,569,035 A | 10/1996 | Balfour et al. | |
| 5,871,356 A | 2/1999 | Guedj | |
| 5,876,202 A | 3/1999 | Berlin | |

(Continued)

FOREIGN PATENT DOCUMENTS

| | | | |
|---|---|---|---|
| CN | 102711654 B | 9/2016 | |
| CN | 108495592 B | * 2/2022 | ......... A61B 17/1615 |

(Continued)

OTHER PUBLICATIONS

Akhbar and Sulong, Surgical Drill Bit Design and Thermomechanical Damage in Bone Drilling: A Review, Jan. 2021, Malaysia.

(Continued)

*Primary Examiner* — Eric S Gibson
(74) *Attorney, Agent, or Firm* — H. Jay Spiegel

(57) ABSTRACT

A method of drilling holes in bone and harvesting bone fragments for bone grafting utilizes a specially designed drill bit having a point angle of 115° to 120°; a lip relief angle approximately 10° to 14°, two or three flutes defining a helix angle from 13° to 17° at a distal end, and a helix angle of 31° to 35° in the proximal direction. The drill bit is rotated at less than 75 rpms, preferably less than 50 rpms. At such a slow rotation speed, cooling fluid is not necessary and the drill bit does not heat up sufficiently to cause necrosis of adjacent tissues. The helix angulation of the proximal portion of the drill bit facilitates harvesting bone fragments, which can be reused in bone grafting.

12 Claims, 8 Drawing Sheets

(56) References Cited

U.S. PATENT DOCUMENTS

| | | | |
|---|---|---|---|
| 5,882,198 A * | 3/1999 | Taylor | A61C 5/42 433/102 |
| 6,007,276 A | 12/1999 | Wardell | |
| 6,032,750 A | 3/2000 | Kersten et al. | |
| 6,045,305 A | 4/2000 | Plummer | |
| 6,179,616 B1 * | 1/2001 | Danger | A61C 3/02 433/165 |
| 6,235,035 B1 | 5/2001 | Boukhris | |
| 6,283,682 B1 | 9/2001 | Plummer | |
| 7,270,541 B1 * | 9/2007 | Johnson | A61C 5/42 433/102 |
| 7,665,989 B2 | 2/2010 | Brajnovic et al. | |
| 8,047,842 B2 * | 11/2011 | Johnson | A61C 5/42 433/102 |
| 8,408,850 B2 * | 4/2013 | George | B24B 3/24 408/230 |
| 8,550,756 B2 | 10/2013 | Borschert et al. | |
| 8,734,068 B2 * | 5/2014 | Krieg | B23B 51/02 408/229 |
| 8,770,974 B2 | 7/2014 | Suter et al. | |
| 9,004,825 B2 * | 4/2015 | Gruber | B23B 51/02 408/1 R |
| 2007/0293867 A1 * | 12/2007 | Anitua | A61C 8/0089 606/80 |
| 2012/0004661 A1 * | 1/2012 | Leppelmeier | A61B 17/1615 606/80 |
| 2015/0057664 A1 * | 2/2015 | Scianamblo | B23B 51/02 606/80 |
| 2021/0220918 A1 | 7/2021 | Plummer | |
| 2024/0156471 A1 * | 5/2024 | Pourati | A61C 1/02 |

FOREIGN PATENT DOCUMENTS

| | | | |
|---|---|---|---|
| WO | WO2007085966 A2 | 1/2006 | |
| WO | WO-2024107793 A1 * | 5/2024 | A61B 17/1615 |

OTHER PUBLICATIONS

Eduardo Anitua, MD, DDS, A Novel Drilling Procedure and Subsequent Bone Autograft Preparation: A Technical Note, vol. 22, No. 1, 2007, The International Journal of Oral.

C Liang, Osteogenic potential of three different autogenous bone particles harvested during implant surgery, 2017 John Wiley & Sons A/S.

* cited by examiner

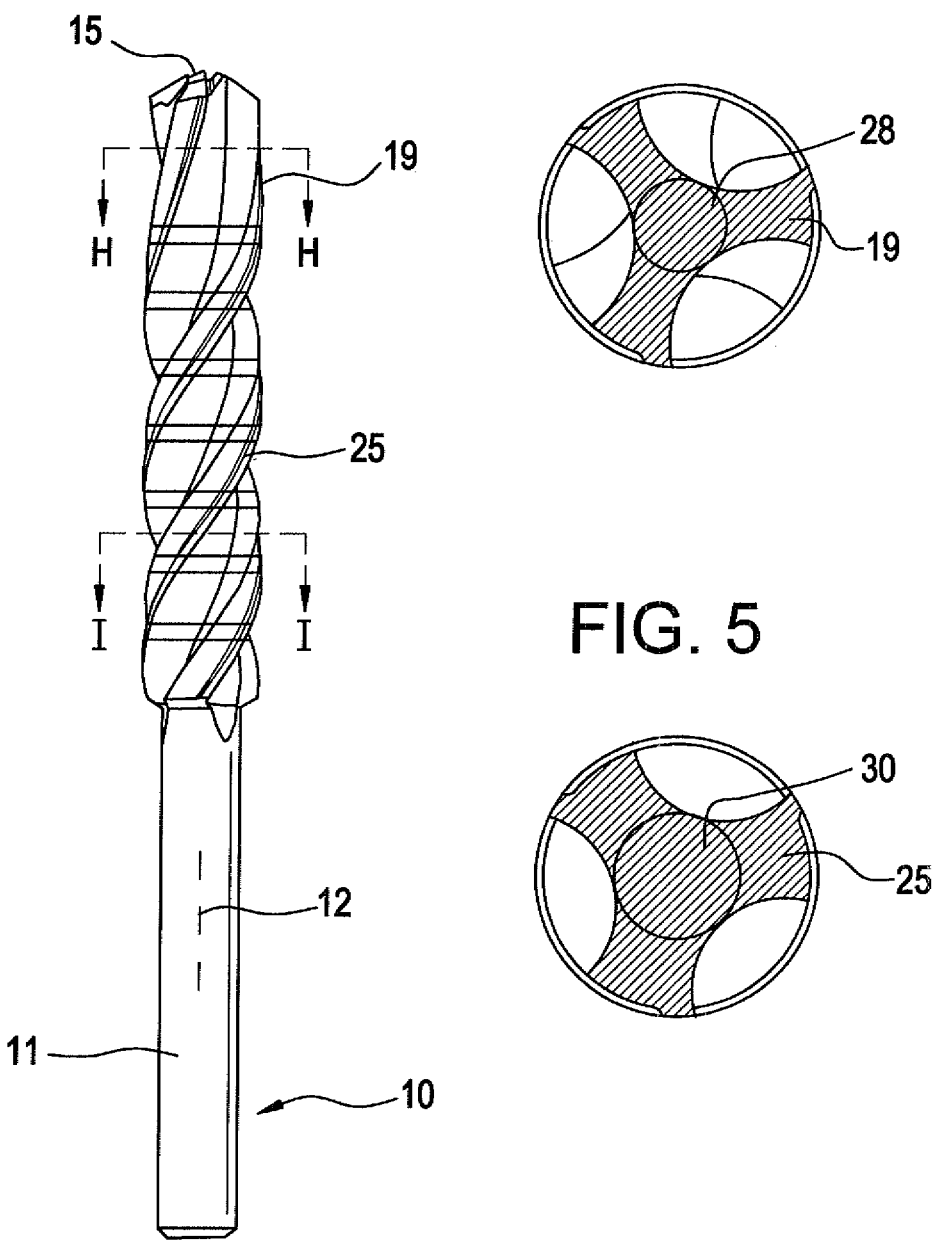

FIG. 8
FIG. 9
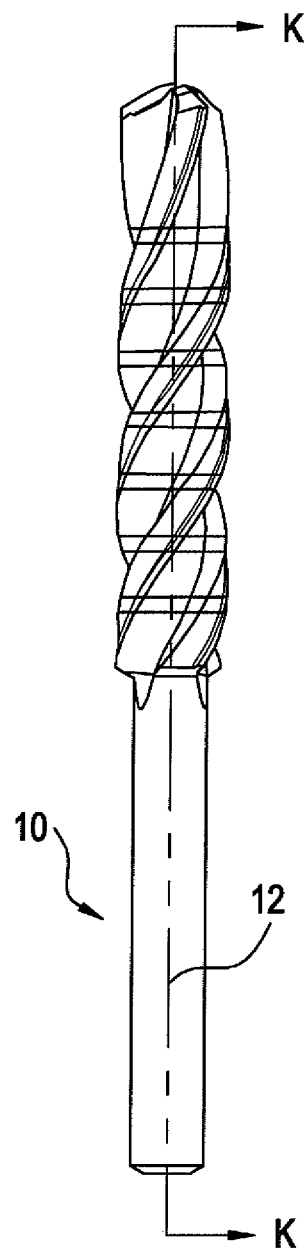
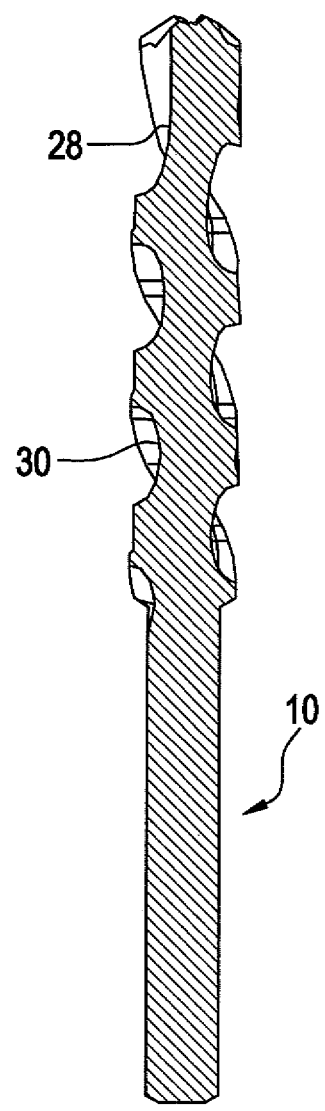

FIG. 15
FIG. 16
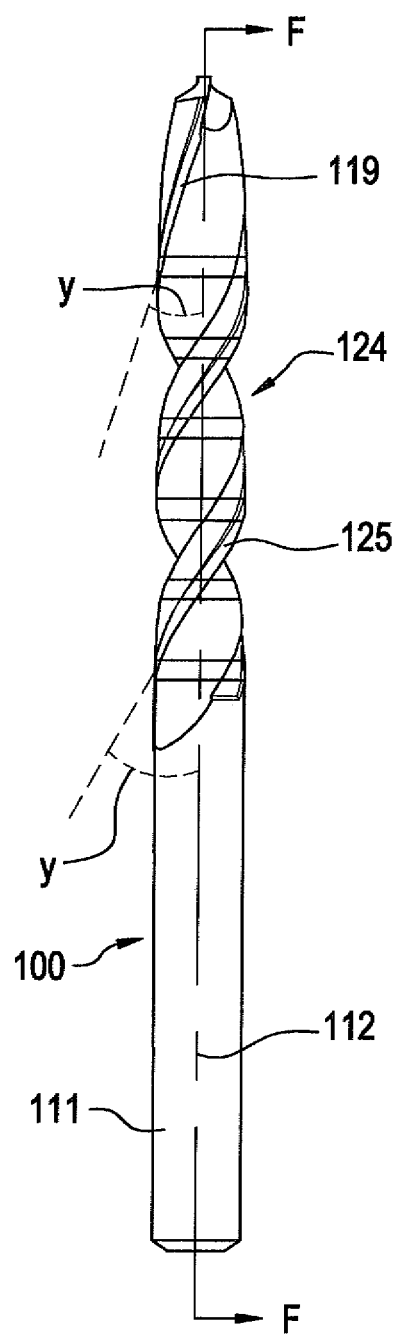
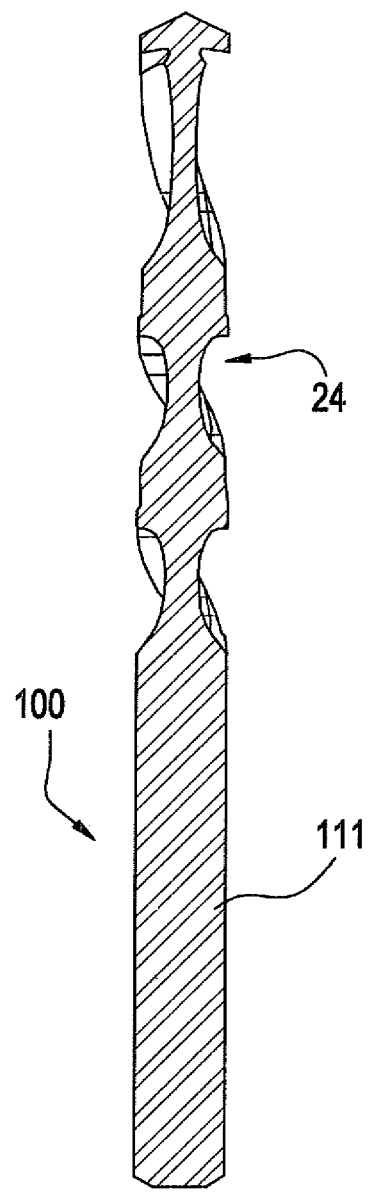

FIG. 17
FIG. 18
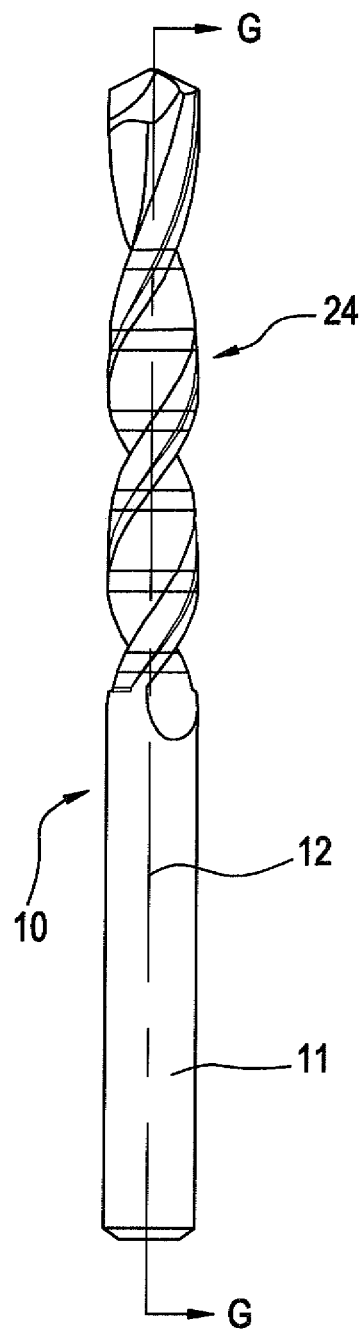
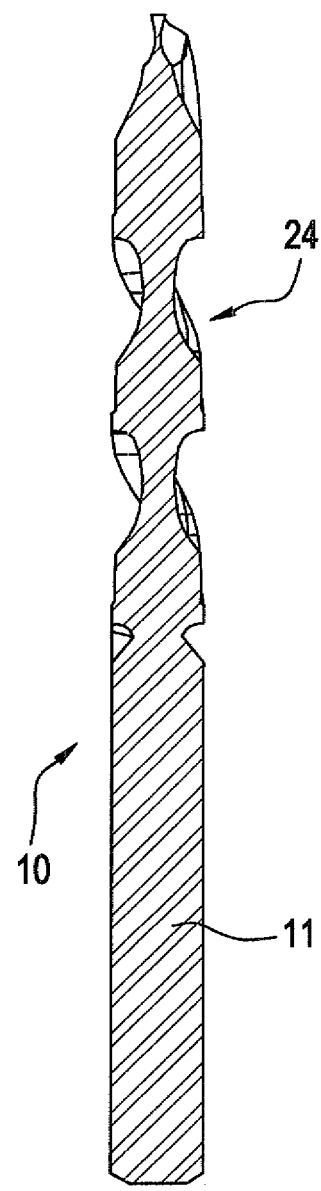

METHOD OF DRILLING HOLES IN BONES AND HARVESTING BONE FRAGMENTS FOR BONE GRAFTING

BACKGROUND OF THE INVENTION

The present invention relates to a method of drilling holes in bones and harvesting bone fragments for bone grafting. The present invention is applicable to dental implant surgery, joint replacement surgery, ligament repairs and replacement, and any other circumstances requiring drilling of a hole in bone.

One circumstance in dentistry is an evolutionary process in which a tooth is afflicted with a cavity also known as caries that requires a filling. Often, eventually, the filling must be replaced with a larger filling or even a crown. Decay under the crown often necessitates removing the tooth and leaving a gap in the person's smile. A dental implant can fill that gap and aesthetically improve the person's smile. Other circumstances include tooth loss through periodontal disease, fracture, pathology or other trauma. Dental implants can also provide extra support for dentures. A dental implant is a fixture that is placed in bone to replicate the function of a tooth's root.

Other circumstances require dental implants such as, for example, where a person is born with one or more baby teeth with no permanent teeth behind them. When the baby teeth fall out, a gap is created that must be filled. Dental implants can serve this purpose.

Other circumstances also exist in which a person may wish to replace their teeth with dental implants for little more than aesthetic reasons. In such circumstances, teeth are pulled and replaced with dental implants. These are examples of circumstances in which one or more holes must be drilled in bone tissue.

In dental implant surgery, it is necessary for the dentist to drill a hole in the Maxilla where the former tooth's or space's location is in the upper bite or in the jaw bone where the former tooth or space was in the lower bite. In either case, typically, a high speed dental drill is employed which may rotate in the range of 500-1,500 rpms or even more. The friction created with a drill bit turning at that speed creates significant heat which could cause necrosis of surrounding tissues. As such, it is necessary for a cooling liquid to be continuously sprayed at the location of the drilling with the fluid with entrained bone fragments being sucked out of the oral cavity using a suction device.

However, in dental implant surgery, the threads of the dental implant need to be fully covered with bone for it to be supported. In cases where the bone around the implant is either missing or insufficient, a bone graft is done. In most cases the bone fragments used to do a bone graft are purchased from bone banks who use allografts (human cadaver), Xenograft (animal other than human), or alloplast (synthetic). There is no chance of tissue rejection since all the harvested bones were sterilized and cleaned where there are no cell. But for the same reason, the grafted material does not have any growth factors or osteogenic capabilities.

It would be advantageous if bone fragments taken from the patient could be employed for this purpose. Thus, there is a need for a technique for drilling such holes which will enable the harvesting of the person's own bone fragments for this purpose. However, at the same time, the large volume of cooling liquid which is employed to cool the site of the drilling and the suction of the liquid including bone fragments removed from the jaw or skull precludes those bone fragments from being reused due to sterilization concerns and the inability to collect them from the suctioned liquid. Autogenous bone has three qualities, it is (1) Osteoconductive (provides a scaffolding for one formation), (2) Osteogenic (containing mesenchymal cells), and (3) Osteoinductive (containing up to 43 growth factors). (See Vertical and Horizontal Ridge Augmentation: New Perspectives, Istavan Uran QUINTESSENCE PUBLISHING CO. 2017, Page 12). Allografts, alloplasts and xenografts have only osteoconductive properties. Harvesting autogenous bone, either in form of block, particulate or shaving most often requires a second surgical site. A second surgical site increases chance of morbidity, complications, and discomfort for a patient. For this reason, most surgeons avoid the second surgical site and including autogenous bone in their grafts.

A technique that could enable the drilling of holes for dental implant surgery while precluding heating of adjacent tissues and facilitating harvesting of bone fragments for reuse would be a significant advance in the techniques of dental implant surgery. It is with these goals in mind that the present invention was conceived and developed.

The following prior art is known to Applicant:

"Surgical Drill Bit Design and Thermomechanical Damage in Bone Drilling: A Review" by Akhbar and Sulong is a printed publication dated January 2021 which goes into great detail in discussing various parameters for the design of surgical drill bits. This reference fails to teach or suggest the speed of rotation, avoidance of cooling liquid, and bone harvesting for reuse taught in the present inventive method.

The following prior art references all teach various types of drill bits including drill bits having varying taper angles. None of these prior art references teaches or suggests the features of the present inventive method. U.S. Pat. No. 1,643,679 to Roderick; U.S. Pat. No. 3,645,642 to Koslow; U.S. Pat. No. 3,667,857 to Shaner et al.; U.S. Pat. No. 4,345,899 to Vlock; U.S. Pat. No. 4,662,803 to Arnold; U.S. Pat. No. 4,913,603 to Friedli et al.; U.S. Pat. No. 5,569,035 to Balfour et al.; U.S. Pat. No. 5,871,356 to Guedj; U.S. Pat. No. 5,876,202 to Berlin; U.S. Pat. No. 6,007,276 to Wardell; U.S. Pat. No. 6,032,750 to Kersten et al.; U.S. Pat. No. 6,045,305 to Plummer; U.S. Pat. No. 6,179,616 to Danger; U.S. Pat. No. 6,235,035 to Boukhris; U.S. Pat. No. 6,283,682 to Plummer; U.S. Pat. No. 7,665,989 to Brajnovic et al.; U.S. Pat. No. 8,408,850 to George; U.S. Pat. No. 8,550,756 to Borschert et al.; U.S. Pat. No. 8,734,068 to Krieg et al.; U.S. Pat. No. 9,004,825 to Gruber; U.S. Pat. No. 8,770,974 to Suter et al.; Published Patent Application No. US 2021/0220918 A1 to Plummer; Published WIPO Application No. WO2007085966A2 to Shuster; and Chinese Publication CN 102711654 B owned by New York University.

SUMMARY OF THE INVENTION

The present invention relates to a method of drilling holes in bone and harvesting bone fragments for bone grafting. The present invention includes the following interrelated objects, aspects and features:

(1) In a first aspect, at the heart of the present invention is a specially designed drill bit usable for creating holes for dental implants. In the preferred embodiment, such a drill bit has a point angle of 115° to 120°. Its lip relief angle is approximately 10° to 14°. Its helix angle is from 13 to 17° at the distal end and transitions to 31° to 35° in the proximal direction. Embodiments of the drill bit having two flutes and three flutes are disclosed.

(2) Applicant has chosen the cited distal helix angle because that angulation has been found to cut a smoother, rounder hole than other angulations. Applicant also found that this angulation shaves the bone off the hole in desirable cone-shaped bony pieces which best facilitates bone grafting using the patient's own bone fragments.

(3) The proximal angulation of 31-35° has been found by Applicant to be ideal for quickly removing bone chips to minimize heat buildup at the drilling site.

(4) One important feature of the present invention is that in order to capture bone fragments for reuse, it is necessary to avoid using a cooling fluid sprayed onto the drill bit during drilling. Applicant found that the only way to facilitate such a procedure is for the drill bit to be rotated at a slow speed, less than 75 rpms, and ideally less than 50 rpms. At such a slow rotation speed, Applicant has found that cooling fluid is not necessary and the drill bit does not heat up sufficiently to cause necrosis of adjacent tissues. Akhbar et al. reported in the prior art reference cited hereinabove that maintaining bone temperature below 47° C. avoids thermal damage in bone drilling. Applicant has found that drilling at the slow speeds mentioned above precludes heating of bone or adjacent tissue above 47° C.

(5) Applicant has found that the helix angulation of the proximal portion of the drill bit in the range of 31-35° is an effective angulation to facilitate harvesting bone fragments. The bone fragments can adhere within the grooves in the drill bit. As such, it is necessary to periodically dip the drill bit into a liquid to facilitate removing the bone chips from the grooves in the drill bit. In this procedure, the drill bit is dipped into the liquid such as a saline solution which can be contained within a container such as a test tube, and a rubber device that can be used to slough off the bone fragments from the drill bit, whereupon drilling can resume. Meanwhile, a screen may be used to pour the liquid through the screen and harvest the bone fragments from the liquid in a sterile manner.

(6) After the drilling has been completed, the dental surgeon will assess whether bone grafting is necessary and the volume of bone graft material that is necessary to be employed. Once the assessment has been completed, the implant is inserted in the prepared hole. Patient's own bone, harvested using the explained procedure, can be used alone or in combination with the other graft materials for best results. Adding the harvested bone with its benefits will improve the healing and quality of the regenerated bone. The harvested bone might also help the soft tissue heal faster and with less discomfort. After these procedures are completed, an implant post can be installed within the hole that has been drilled in a manner well understood by those skilled in the art.

As such, it is a first object of the present invention to provide a method of drilling holes in bone and harvesting bone fragments for later use in bone grafting.

It is a further object of the present invention to provide such a method in which a specially designed drill bit is utilized in drilling holes for applications including but not limited to dental implant purposes.

It is a still further object of the present invention to provide such a method in which the drill bit is specially designed to be able to be turned slowly, preferably below 50 rpms while avoiding heating adjacent tissues with the resultant necrosis.

It is a yet further object of the present invention to provide such a method in which cooling liquid is not required while the drill bit is drilling the hole at slow speed.

It is a still further object of the present invention to provide such a method in which the patient's own bone fragments are harvested by the drill bit and retained for use in future bone grafting.

It is a still further object of the present invention to provide such a method in which a tube containing saline solution is utilized with the drill bit periodically dipped into the saline solution to remove bone fragments therefrom which have been adhering to the drill bit.

It is a still further object of the present invention to provide an appliance that may be run along the length of the drill bit to assist in removing bone fragments therefrom.

These and other objects, aspects and features of the present invention will be better understood from the following detailed description of the preferred embodiments when read in conjunction with the appended drawing figures.

BRIEF DESCRIPTION OF THE DRAWINGS

FIG. 1b shows an end view of the drill bit of FIG. 1a.

FIG. 3 shows a further side view of the first embodiment of the inventive drill bit.

FIG. 4 shows a cross-sectional view along the line H-H of FIG. 3.

FIG. 5 shows a cross-sectional view along the line I-I of FIG. 3.

FIG. 8 shows a further side view of the first embodiment of the inventive drill bit.

FIG. 9 shows a longitudinal cross-sectional view along the line K-K of FIG. 8.

FIG. 15 shows a further side view of the second embodiment of the inventive drill bit.

FIG. 16 shows a longitudinal cross-sectional view along the line F-F of FIG. 15.

FIG. 17 shows an additional side view of the second embodiment of the inventive drill bit.

FIG. 18 shows a cross-sectional view along the line G-G of FIG. 17.

SPECIFIC DESCRIPTION OF THE PREFERRED EMBODIMENTS

Figure 1B:
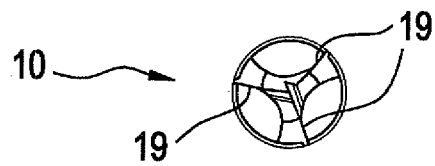
Figure 1A:
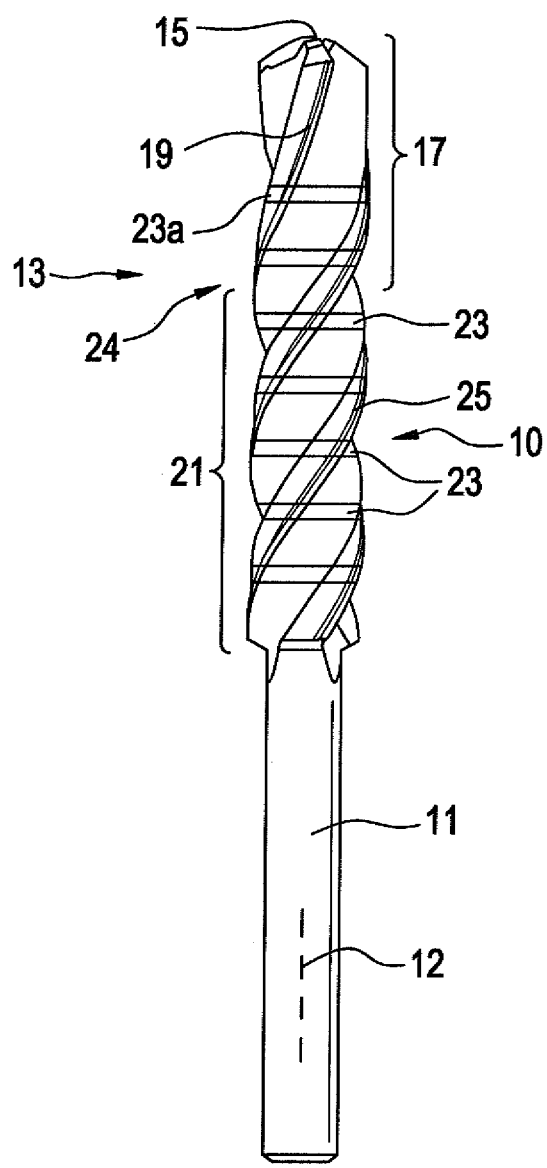
FIG. 1a shows a side view of a first embodiment of drill bit utilized in accordance with the teachings of the present invention including three flutes.
Figure 2:
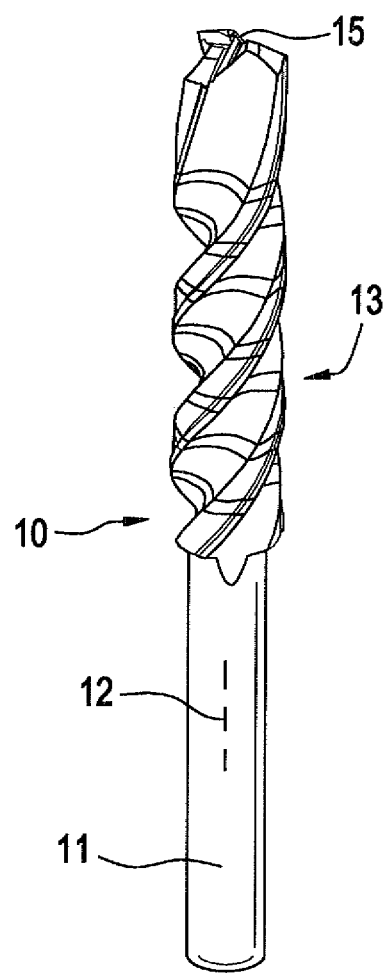
FIG. 2 shows the drill bit of FIGS. 1a and 1b rotated from the orientation shown in FIG. 1.

With reference first to FIGS. 1a, 1b and 2-10, a first embodiment of the inventive drill bit incorporated into the present invention is generally designated by the reference numeral 10. The bit has a shank 11 and a distal portion 13 with structures designed to allow the drilling of a hole. These structures include a distal end 15 which is pointed with a point angle of 116° to 120° preferably 118°, and a first drilling portion shown by the bracket 17 in FIG. 1a defining a first region which includes three cutting edges 19 which displace an angle of 13° 17° with respect to the axis of elongation of the bit which is designated by the reference numeral 12. In this embodiment of the present invention, the angulation of the cutting edges 19 is 15° with respect to the axis of elongation 12 of the bit 10. As shown in FIG. 1b, there are three cutting edges displaced 120° apart about the circumference of the bit 10.

Markings 23 are provided at spaced locations about the bit 10 so that the surgeon can determine the depth of penetration of the bit 10 within the bone structure of the patient. In one embodiment, the first marking 23a is approximately 4 millimeters proximal of the distal tip 15 of the bit 10. Further markings proximal of the marking 23a are, in a preferred configuration, spaced 2 mm apart.

There is a transition between the cutting edges 19 or flutes and the more proximal cutting edges 25 where the brackets 17 and 21 are adjacent one another. The transition after reference numeral 24 is smooth to prevent a sharp bend in the flutes that would cause bone chip buildup. The angulation of the cutting edges or flutes 25 in a second region with respect to the axis of elongation 12 of the bit 10 is within the range of 31° to 35° and preferably approximately 33°. Applicant has found that the angulation of the cutting edges 19 at the distal end of the bit 10 provides extra rigidity and strength for a smoother, rounder hole formation. The greater angulation of the proximal cutting edges or flutes 25 best facilitates rapid removal of bone chips to substantially reduce heat buildup, particularly, as the bit 10 is rotated at an extremely slow speed, preferably less than 50 rpms.

FIGS. 3-5 show further details of the first embodiment of the inventive drill bit 10. In particular, when comparing the cross-sections of FIGS. 4 and 5, the cross-section shown in FIG. 4 which shows the flutes 19, it should be evident that those flutes are thinner than the flutes 25 shown in the cross-section of FIG. 5. Also notable is the web thickness near the tip of the drill which is shown by the circle 28 as compared to the web thickness proximally where the flutes 25 are located which is designated by the reference numeral 30. This difference in web thickness is also clearly shown in FIG. 7 which shows the thicker area 30 as compared to the thinner area 28. Also notable are the differing flute shapes shown at 28 and 30 in FIG. 9.

Figure 10:
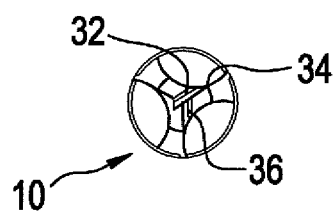
FIG. 10 shows an end view of the first embodiment of the inventive drill bit slightly rotated from the view of FIG. 1b.
Figure 6:
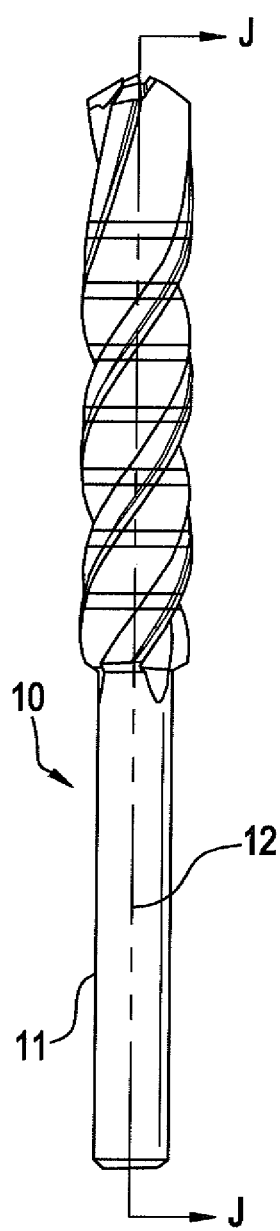
FIG. 6 shows a further side view of the first embodiment of the inventive drill bit.
Figure 7:
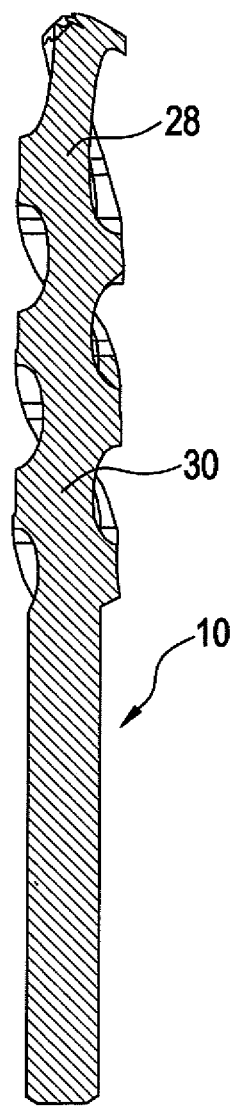
FIG. 7 shows a longitudinal cross-sectional view along the line J-J of FIG. 6.

FIG. 10 shows a tertiary cutting edge 32 which stops just short of the centerline of the bit 10 with a secondary cutting edge 34 stopping just short of center while a primary cutting edge 36 extends all the way to the center of the bit 10.

FIGS. 11-18 show a second embodiment of the inventive drill bit which differs from the first embodiment in that it has two flutes rather than three. These figures show the bit 100 with shank 111, axis of elongation 112, tip 115, flutes 127, web portion 129.

A round 2-4 mm round burr is used to make an initial hole to prevent "walking" of the tip.

Figure 11:
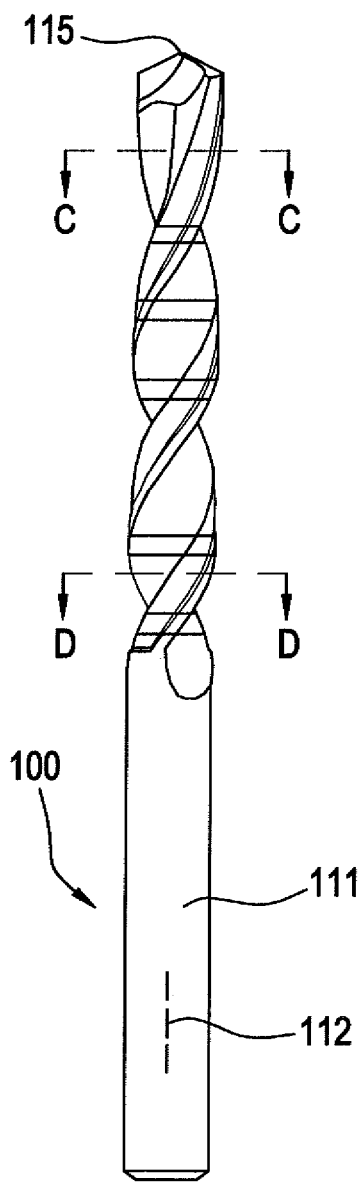
FIG. 11 shows a side view of a second embodiment of the inventive drill bit having two flutes.
Figure 12:
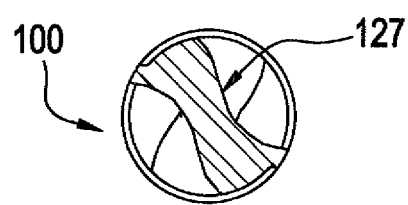
FIG. 12 shows a cross-sectional view along the line C-C of FIG. 11.

As shown in FIG. 12, which is a cross-section along the line C-C of FIG. 11, the curvature of the flutes at 127 is characteristic of parabolic flutes as opposed to typical flutes which straighten out at this point rather than curving back. Applicant has found that this configuration best facilitates cutting of a circular cross-section hole.

Figure 13:
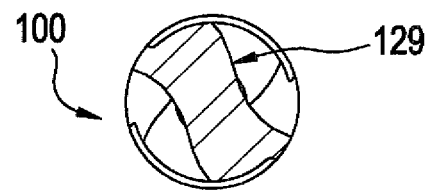
FIG. 13 shows a cross-sectional view along the line D-D of FIG. 11.
Figure 14:
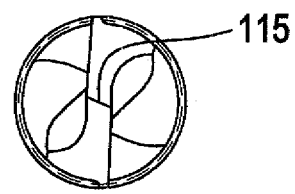
FIG. 14 shows an end view of the drill bit of FIG. 11.

FIG. 13, which shows a cross-sectional view along the line D-D of FIG. 11, shows at the location of the cross-section a web portion 129 which is thicker than the web portion 127 shown in FIG. 12, and more distally. Applicant has found that this thicker portion helps to facilitate collection of bone chips in an efficient manner during the drilling process.

FIGS. 15-18 accurately show the transition area 124 between the angulation at the distal end of the bit 100 and the angulation more proximally. FIG. 15 shows the angle X between the cutting edges or flutes 125 and the axis 112 of elongation of the bit 100. As explained above, the angle X is within the range of 31° to 35° and preferably 33°. FIG. 15 also shows the angle Y between the cutting edges or flutes 119 and the axis 112.

The inventive drill as explained above with reference to FIGS. 1a-18 is utilized in performing the method comprising the present invention. In the inventive method, the patient is prepped for the required surgical procedure utilizing whatever anesthetic is necessary based upon the particular procedure that is being undertaken, whether dental surgery, joint replacement, ligament repair or replacement, or any other.

The area where a hole is to be drilled is accessed. The drill bit 10 or 100 is attached to a suitable drill device (not shown) and is rotated at a speed less than 50 rpms. A 2-4 mm burr is first used to create a small hole. Then, the tip 15 or 115 of the drill bit 10 or 100 is engaged with the bone surface at the hole where drilling is to take place. Due to the hole formed by the burr, the drill bit tip is unlikely to "walk" laterally away from the preferred location for drilling. The distal helical cutting edges 19 or 119 ensure that the hole to be drilled will be circular in cross section.

As the bit 10 is advanced forward, the markings 23 about the periphery of the bit 10 inform the surgeon of the depth to which the bit 10 has been advanced. As the bit advances proximally of the area 17 (FIG. 1a) and into the more proximal area 21, the angulation of the cutting edges 25 facilitates harvesting of bone fragments and particles in an efficient manner, carving those fragments and particles out from the bone structure.

Figure 19:
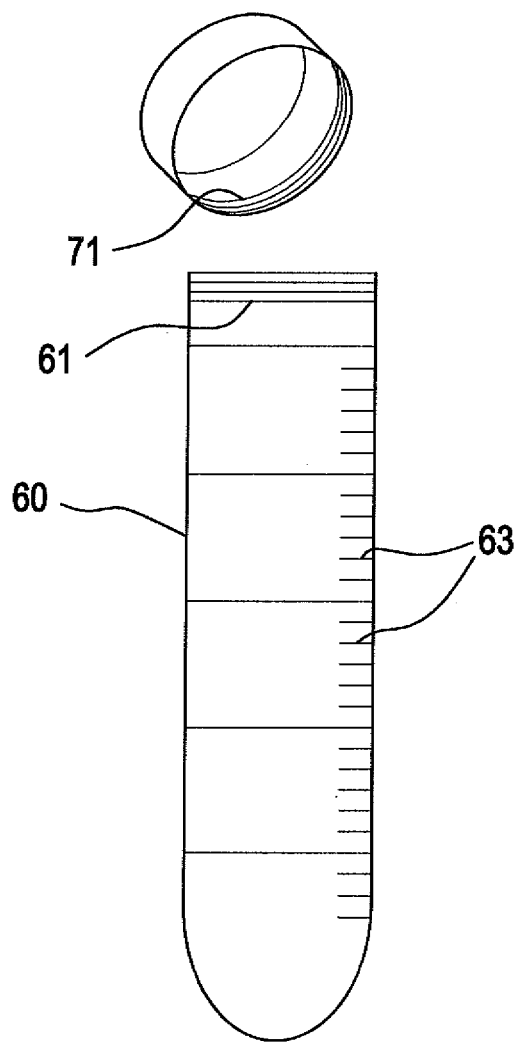
FIG. 19 shows a side view of a tube used to harvest bone fragments.
Figure 20:
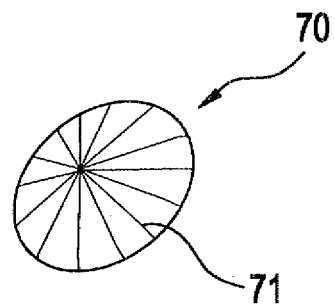
FIG. 20 shows a top view of a screw cap for the tube of FIG. 19.

If desired, a container like a test tube 60 as shown in FIG. 19 may be filled with a liquid such as saline solution and periodically the bit 10 or 100 may be dipped into the saline solution to facilitate sloughing off of the bone particles and shavings. A rubber top 70 with a plurality of radial slits 71 therethrough (FIG. 20) may be used with the periphery of the hole being sized to engage the recesses between the cutting edges to facilitate removing bone particles and fragments from the drill bit. The rubber top may be periodically sterilized. The tube 60 and top 70 may have complimentary threads 61 and 71, respectively, to allow the top 70 to be threaded onto the tube 60. The tube 60 may have gradations 63 printed thereon to enable measurement of the volume of bone fragments collected. The saline solution with the bone particles and fragments therein may be poured through a screen or other filter to remove the bone particles and fragments and complete the harvesting process. The drill bit may be re-engaged with the hole partially formed and may be advanced while rotating at less than 50 rpms until the marking 23 corresponding to the desired depth of penetration has been reached, whereupon the drill bit may be reversed out of the hole and any remaining bone fragments may be removed therefrom in the manner described above.

If desired, and necessary, where bone grafts are necessary, bone particles and fragments harvested from the hole formed by the drill bit 10 may be reused in a suitable manner to add a bone graft.

Applicant has found that the angulations of the proximal and distal cutting edges of the drill bit result in the ability to form a precise circular cross section hole while harvesting bone fragments and particles, with the drill bit rotating at less than 75 rpms, preferably less than 50 rpms, and with no requirement for a cooling liquid to be sprayed at the location of the drilling which facilitates the harvesting of bone particles and fragments. In this way, necrosis of adjacent tissues and "burning" of bone fragments and particles are precluded. The present invention solves an important issue in drilling of holes during surgical procedures by facilitating safe drilling without need for cooling liquid while enhancing the accuracy of drilling, including facilitating circular cross section holes and while permitting the patient's own bone fragments and particles to be reused in any bone grafts that are required.

Use of the inventive method has several additional advantages including avoiding perforation of cortical plates, ability to gain access to the sinus floor during dental surgery without perforating the Schnedarian membrane and minimal reduction of bone while preparing a site for a dental implant which helps facilitate primary stability in medullary/soft bone. Without need for use of cooling liquid, visibility at the site of drilling is enhanced.

Applicant has also found that the shavings of bone resulting from practicing of the inventive method are often cone-shaped bony pieces which Applicant has found have a superior grafting ability as compared to smaller chopped up particulate bone obtained when other drills are employed.

As explained above, the angulation of the cutting edges in the proximal end of the drill bit 10, in the range of 31°-35°, preferably 33°, helps facilitate retaining the removed bone material for later harvesting using, for example, a test tube filled with saline solution.

As such, an invention has been disclosed in terms of preferred embodiments thereof which fulfill each and every one of the objects of the invention as set forth hereinabove, and provides a new and useful method of drilling holes in bones and harvesting bone fragments for bone grafting of great novelty and utility.

Of course, various changes, modifications and alterations in the teachings of the present invention will be better understood by those skilled in the art without departing from the intended spirit and scope thereof.

As such, it is intended that the present invention only be limited by the terms of the appended claims.

The invention claimed is:

1. A method of drilling a hole in a bone including the steps of:
   a) providing a drill bit configured to drill a hole in a bone, said hole having a desired cross-section;
   b) rotating said drill bit at a rotation speed less than 75 revolutions per minute (rpm) while advancing said drill bit to drill said hole;
   c) said rotating step being carried out without use of cooling liquid;
   d) harvesting bone fragments created from said rotating and advancing step;
   e) wherein said drill bit includes a distal pointed tip, a first region proximal of said tip with helical cutting edges defining a first angulation of 13°-17° with respect to an axis of elongation of said drill bit, and a second region proximal of said first region with helical cutting edges defining a second angulation of 31° to 35° with respect to said axis of elongation; and
   f) further including the step of periodically dipping said drill bit into a body of liquid to facilitate removal of bone fragments therefrom.

2. The method of claim 1, wherein said pointed tip defines a point angle of 116° to 120°.

3. The method of claim 1, wherein there are a number of helical cutting edges in said first and second regions chosen from the group consisting of two or three helical cutting edges, said helical cutting edges being equally spaced about a circumference of said drill bit.

4. The method of claim 1, wherein said drill bit includes a proximal shank adapted to be coupled to a drill for facilitating rotation of said drill bit.

5. The method of claim 1, said first angulation being 15°, said second angulation being 33°, and said tip having an angulation of 118°.

6. The method of claim 1, wherein said liquid comprises a saline solution.

7. The method of claim 6, wherein said saline solution is contained within a container.

8. The method of claim 1, wherein said drill bit has a smooth transition of said cutting edges from said first region to said second region.

9. The method of claim 1, wherein said rotation speed is less than 50 rpms.

10. A method of drilling a hole in a bone including the steps of:
    a) providing a drill bit configured to drill a hole in a bone, said hole having a desired cross-section, said drill bit including a distal pointed tip with a 116° to 120° angulation, a first region proximal of said tip with two or three equally spaced helical cutting edges defining a first angulation of 13° to 17° with respect to an axis of elongation of said drill bit, and a second region proximal of said first region with three equally spaced helical cutting edges defining a second angulation of 31° to 35° with respect to said axis of elongation;
    b) rotating said drill bit at a rotation speed less than 75 revolutions per minute (rpm) while advancing said drill bit to drill said hole;
    c) said rotating step being carried out without use of cooling liquid;
    d) harvesting bone fragments created from said rotating and advancing step; and
    e) further including the step of periodically dipping said drill bit into a body of saline solution to facilitate removal of bone fragments therefrom.

11. The method of claim 10, said first angulation being 15°, said second angulation being 33°, and said tip angle being 118°.

12. The method of claim 10, wherein said drill bit has a smooth transition of said cutting edges from said first region to said second region.

* * * * *